United States Patent [19]

Harbert et al.

[11] 4,217,355
[45] Aug. 12, 1980

[54] AMIDE THERAPEUTIC AGENTS

[75] Inventors: Charles A. Harbert, Waterford; Joseph G. Lombardino, Niantic, both of Conn.

[73] Assignee: Pfizer Inc., New York, N.Y.

[21] Appl. No.: 899,065

[22] Filed: Apr. 24, 1978

[51] Int. Cl.$^2$ .......................................... C07D 277/38
[52] U.S. Cl. .................................... 424/270; 548/185
[58] Field of Search ................ 260/306.8 R; 424/270; 548/185

[56] References Cited

U.S. PATENT DOCUMENTS

| | | | |
|---|---|---|---|
| 3,553,227 | 1/1971 | Westland | 260/306.8 |
| 3,853,862 | 12/1974 | Lombardino | 260/306.8 R |
| 3,862,167 | 1/1979 | Veno et al. | 260/306.8 R |
| 3,957,812 | 5/1976 | Rossignol et al. | 260/306.8 R |

OTHER PUBLICATIONS

Lombardino et al., Jour. of Heterocyclic Chemistry, vol. 13, p. 333 (1976).

Primary Examiner—Nicholas S. Rizzo
Attorney, Agent, or Firm—Connolly and Hutz

[57] ABSTRACT

A series of N-(2-thiazolyl)amides has been prepared, including their pharmaceutically acceptable acid addition salts as well as pharmaceutical compositions containing same. These compounds are useful in therapy as anti-inflammatory agents in addition to being useful as immunoregulatory agents for modulating various body immune responses. Preferred member compounds include N-(2-thiazolyl)-α-methylaminoacetamide, N-(2-thiazolyl)-α-benzylaminoacetamide, N-(2-thiazolyl)-α-(p-fluorobenzylamino)acetamide, N-(2-thiazolyl)-α-(2-thenylamino)acetamide and N-(4-methyl-2-thiazolyl)-α-amino-β-phenylpropionamide, and their hydrohalide acid addition salts. Three different methods of preparation are provided and these are all described in some detail, including the various synthetic routes leading to the required novel intermediates and/or starting materials.

24 Claims, No Drawings

AMIDE THERAPEUTIC AGENTS

BACKGROUND OF THE INVENTION

This invention relates to new and useful N-(2-thiazolyl)amides in the field of medicinal chemistry. More particularly, it is concerned with a novel series of N-(2-thiazolyl)amide compounds, which are of especial value in view of their ability to alleviate inflammatory conditions and regulate body immune responses. The invention also includes various novel pharmaceutical compositions within its scope.

In the past, various attempts have been made by numerous investigators in the specialized field of synthetic organic medicinal chemistry to obtain new and useful anti-inflammatory agents. For the most part, these efforts have involved the synthesis and testing of various steroidal hormone compounds such as the corticosteroids or non-steroidal substances of an acidic nature such as phenylbutazone, indomethacin and the like. However, in the search for still newer and better or more improved anti-arthritic agents, far less is known about the effect of basic or neutral non-steroidal agents in this area, albeit this would be attractive since they might well lack the untoward steroidal side-effects in additiion to possessing other useful advantages normally associated with most acidic, non-steroidal compounds.

SUMMARY OF THE INVENTION

In accordance with the present invention, it has now been rather surprisingly found that certain novel N-(2-thiazolyl)amides are extremely useful when employed in the field of therapy as non-steroidal therapeutic agents for alleviating inflammatory conditions as well as for regulating body immune responses. More specifically, the novel compounds of this invention are all selected from the group consisting of N-(2-thiazolyl)amides of the formulae:

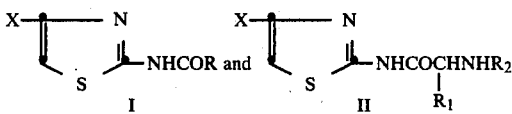

and the pharmaceutically acceptable acid addition salts thereof, wherein X is a member selected from the group consisting of hydrogen and alkyl having from one to six carbon atoms; R is a member selected from the group consisting of 2-pyrrolidinyl, 2-piperidyl, 2-homopiperidyl, 3-morpholinyl and 3-thiomorpholinyl; $R_1$ is a member selected from the group consisting of hydrogen, alkyl having from one to four carbon atoms, benzyl and β-phenylethyl; and $R_2$ is a member selected from the group consisting of hydrogen, cyclooctyl, cycloalkylmethyl having from five to seven carbon atoms in the cycloalkyl moiety, naphthylmethyl, picolinyl, furfuryl, tetrahydrofuranyl, thenyl, phenylalkyl and ring-substituted phenylalkyl each having up to three carbon atoms in the alkyl moiety wherein said ring substituent, when divalent, is methylenedioxy or ethylenedioxy, directly attached to adjacent positions of the phenyl ring and when monovalent is a member chosen from the group consisting of fluorine, chlorine, bromine, trifluoromethyl, lower alkyl and lower alkoxy (each having up to three carbon atoms); said $R_2$ being other than hydrogen when said $R_1$ is hydrogen or alkyl having from one to four carbon atoms.

According to the present invention, there is also provided various novel pharmaceutical compositions useful for alleviating inflammatory responses comprising a pharmaceutically acceptable carrier and a therapeutically-effective amount of a compound selected from the group consisting of N-(2-thiazolyl)amides of the formula:

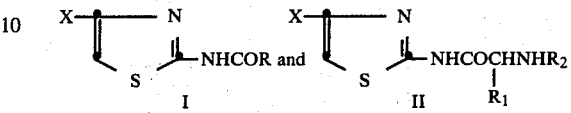

and the pharmaceutically acceptable acid addition salts thereof, wherein X is a member selected from the group consisting of hydrogen and alkyl having from one to six carbon atoms; R is a member selected from the group consisting of 2-pyrrolidinyl, 2-piperidyl, 2-homopiperidyl, 3-morpholinyl and 3-thiomorpholinyl; $R_1$ is a member selected from the group consisting of hydrogen, alkyl having from one to four carbon atoms, benzyl and β-phenylethyl; and $R_2$ is a member selected from the group consisting of hydrogen, alkyl having from one to six carbon atoms, allyl, methallyl, cyclooctyl, cycloalkylmethyl having from five to seven carbon atoms in the cycloalkyl moiety, naphthylmethyl, picolinyl, furfuryl, tetrahydrofuryl, thenyl, phenylalkyl and ring-substituted phenylalkyl each having up to three carbon atoms in the alkyl moiety wherein said ring substituent, when divalent, is methylenedioxy or ethylenedioxy directly attached to adjacent positions of positions of the phenyl ring and when monovalent is a member chosen from the group consisting of fluorine, chlorine, bromine, trifluoromethyl, lower alkyl and lower alkoxy.

All the compounds of this invention are useful in alleviating the painful effects caused by various inflammatory conditions, in addition to being useful as immunoregulator agents for modulating various body immune responses. Compounds of formula II where X and $R_1$ are each hydrogen and $R_2$ is methyl, ethyl, n-propyl and isopropyl are all known from the disclosure of J. G. Lombardino in U.S. Pat. No. 3,853,862, where they are reported to be useful as intermediate leading to the production of certain non-steroidal anti-inflammatory N-(2-thiazolyl)-3,4-dihydro-2-alkyl-4-oxo-2H-1,2-benzothiazine-3-carboxamide 1,1-dioxides previously discussed in U.S. Pat. No. 3,591,584. However, the novel method of using these compounds, including their novel pharmaceutical compositions, as described in this invention has never before been contemplated by the prior art.

Of especial interest in this connection are such typical and preferred member compounds of the invention as N-(2-thiazolyl)-α-methylaminoacetamide, N-(2-thiazolyl)-α-benzylaminoacetamide, N-(2-thiazolyl)-α-(p-fluorobenzylamino)acetamide, N-(2-thiazolyl)-α-(2-thienylamino)acetamide and N-(4-methyl-2-thiazolyl)-α-amino-β-phenylpropionamide, and their hydrobromide and hydrochloride acid addition salts. These particular compounds are all highly potent as regards their anti-inflammatory activity, in addition to being extremely effective in regulating body immune responses. Except for N-(2-thiazolyl)-α-methylaminoacetamide (where X=H; $R_1$=H and $R_2$=CH$_3$), the preferred amides are, as previously indicated, new compounds.

DETAILED DESCRIPTION OF THE INVENTION

In accordance with the process employed for preparing the compounds of this invention, 2-aminothiazole or a suitable 4-alkyl derivative thereof (where X is as previously defined) is condensed with an appropriately substituted α-aminoacid of the formula RCOOH or $HN(R_2)CH(R_1)COOH$ wherein R, $R_1$ and $R_2$ are all as previously defined. In this connection, it is to be noted that even though substantially equimolar amounts of reactant and reagent are normally employed in carrying out the aforesaid process (a slight excess of the 2-aminothiazole component is usually preferred), the free amino group of the α-aminoacid component must first preferably be protected by conventional blocking techniques (e.g., by a carbobenzyloxy group) before undergoing the condensation reaction. The latter reaction is generally conducted in a reaction-inert polar organic solvent, such as tetrahydrofuran or dioxane, and in the presence of at least an equimolar amount of suitable coupling agent or promoter (a slight to moderate excess is usually employed) like N-ethoxycarbonyl-2-ethoxy-1,2-dihydroquinoline (EEDQ), dicyclohexylcarbodiimide, N,N'-carbonyl-diimidazole or phosphorus oxychloride at a temperature that in the range of from about 20° C. up to about 150° C. for a period of about two to about 24 hours. Upon completion of the aforesaid condensation step leading to the corresponding "blocked" amide, the blocking group is then removed by conventional means (e.g., by hydrogenolysis or the use of a strong mineral acid) to yield the desired N-(2-thiazolyl)amide.

The starting materials required for preparing the N-(2-thiazolyl)amide compounds by the process of this invention are, for the most part, known compounds and are either readily available commercially, like 2-aminothiazole and N-benzyloxycarbonyl-N-methylglycine, or else they can easily be synthesized by those skilled in the art starting from common chemical reagents and using conventional methods of organic synthesis. For instance, the 4-alkyl derivatives of 2-aminothiazole can all be synthesized by reacting the corresponding α-haloketone compound with thiourea in accordance with the general organic procedures set forth by Elderfield et al, in "Heterocyclic Compounds", Vol. 5, John Wiley & Sons, Inc., New York, N.Y. (1957), p. 496 ff. The N-benzyloxycarbonyl aminoacids, on the other hand, are all readily prepared by the general synthetic methods previously reviewed by Greenstein and Winitz in "Chemistry of the Amino Acids", Vols. 1–3, John Wiley & Sons, Inc., New York, N.Y. (1961).

An alternate and preferred method of synthesis for preparing those compounds of the invention having structural formula II simply involves (1) treating the corresponding 2-aminothiazole starting material, as previously defined, with an appropriately substituted α-haloalkanoyl halide of the formula $YCH(R_1)COY$, where the symbol Y represents either chlorine or bromine and $R_1$ is defined as aforesaid and is preferably hydrogen, followed by (2) reaction of the resulting 2-(α-haloalkanoylamino)thiazole intermediate with an appropriate organic amine of the formula $R_2NH_2$, with $R_2$ again having the same meaning as before.

In connection with a more detailed consideration of the preferred process of this invention, it is to be noted that the first reaction step is preferably carried out by reacting the 2-aminothiazole and α-haloalkanoyl halide components in a reaction-inert organic solvent such as an aromatic hydrocarbon solvent like benzene, toluene, xylene and so on, preferably using an excess of the heterocyclic amine base (e.g., at least a one molar excess) with respect to the required equimolar reaction ratio. The temperature at which the reaction can be conducted varies widely and generally lies within the range of from about 20° C. up to 140° C. for a period of about one-half to about ten hours. A preferred reaction time and temperature for the process would be one that is approximately 65°–80° C. for about 1–2 hours. Upon completion of the reaction, the desired product is readily recovered from the reaction mixture by conventional means, e.g., by filtration of the mixture to remove amine hydrohalide by-product, followed by evaporation of the reaction solvent to afford a concentrate or solid residue that can be subsequently purified by means of trituration with a suitable solvent like methylene chloride and/or column chromatography if necessary.

Conversion of the 2-(α-haloalkanoylamino)thiazole thus produced to the corresponding N-(2-thiazolyl)amide compound is then effected by reacting said halo intermediate with an appropriate amine base of the formula $R_2NH_2$, where $R_2$ is as previously defined, to form the desired final product of structural formula II. This particular reaction is normally carried out by using an excess of the organic amine base with respect to the required equimolar ratio, since this serves to shift the reaction equilibrium to the product side of the equation. In addition, the excess amine can also function as a solvent for the reaction, with a preferred excess for these purposes being from about two to about ten moles of amine per one mole of halo intermediate. Nevertheless, it is usually preferable in practice to employ a reaction-inert polar organic solvent for the reaction and this would ordinarily call for the use of such solvents as a lower alkyl ketone like acetone and methyl ethyl ketone or a lower alkanol like methanol, ethanol and isoamyl alcohol, etc., or even a cyclic ether such as dioxane and tetrahydrofuran. The temperature at which the reaction can be conducted varies widely and generally falls within the temperature range of from about 40° C. up to about 150° C. for a period of about one-half to about 12 hours. A preferred reaction time and temperature for the process would be about 50°–90° C. for about 2–4 hours. In the case where a particular solvent is used and/or the boiling point of the amine is below the desired reaction temperature range, it is often customary in practice to employ a sealed pressure vessel in which to conduct the reaction. Upon completion of this step, the desired amide final product is then readily isolated by any number of conventional means, e.g., by evaporation of the solvent from the reaction mixture, followed by extraction of the solid residue with diethyl ether, etc., and subsequent treatment of the ethereal solution with a hydrohalide gas to afford the corresponding crystalline salt.

The starting materials used in preparing the particular N-(2-thiazolyl)amides contemplated by the preferred alternate route of this invention are compounds which are either commercially available or else well known to those skilled in the art. For instance, the α-haloalkanoyl halides used in the first reaction step of the aforesaid route (together with the previously discussed 2-aminothiazole starting materials) are, for the most part, commercially available like bromoacetyl bromide or chloroacetyl chloride, or else they are easily prepared by those skilled in the art from more commonly available reagents such as the corresponding lower alkanoic acids from which they are ultimately derived (e.g., α-bromopropionyl bromide is most conveniently prepared from propionic acid via a simple adaption of the well-known Hell-Volhard-Zelinsky technique, using phosphorus tribromide as the specific halogenating agent of chloice). Additionally, the organic amines ($R_2NH_2$) employed as reagents in the second step of aforesaid two-step reaction process are also, for the most part, known compounds which are either available commercially, like benzylamine, or else of such a nature that they can easily be synthesized by those skilled in the art starting from more readily available reagents (usually the corresponding bromides), using the standard techniques and/or conventional procedures of organic chemistry deemed to be appropriate under these circumstances.

As regards those particular N-(2-thiazolyl)amide compounds of the invention where $R_2$ of structural formula II is other than hydrogen or cyclooctyl, still another alternate route or method of synthesis leading to said compounds is available and this simply involves treating the corresponding amide compound where $R_2$ is hydrogen (prepared by either of the two methods described previously) with a suitable organic halide of the formula $R_2Z$, where $R_2$ is as earlier defined (except for the fact that it is not hydrogen or cyclooctyl) and Z is chlorine, bromine or iodine, in the presence of a base that serves as a hydrogen halide acceptor for the present purposes at hand. This particular reaction is normally carried out in a reaction-inert polar organic solvent of much the same type as that earlier employed in reaction step (2) of the previously discussed principal alternate route and preferably, in a lower alkanol solvent like methanol, ethanol and isoamyl alcohol, etc., containing a minor proportion of a lower dialkyl ether such as diethyl ether and the like. The temperature at which the reaction can be conducted varies within the range of from about 20° C. up to about 130° C. over a period of about 0.5 to about 30 hours, with the preferred reaction time and temperature being one that is generally in the range of about 65°-90° C. for a period of approximately 18-24 hours. In practice, an excess of the unsubstituted N-(2-thiazolyl)amide component is usually employed with respect to the organic halide reagent even though an equimolar reaction is normally called for, since this tends to decrease the possibility of unwanted by-product formation (e.g., a disubstituted product) in addition to shifting the reaction equilibrium to the product side of the equation. For these purposes, at least about a one molar excess of the starting amide with respect to the organic halide reagent will normally suffice. Moreover, in the case of those organic halides that are somewhat volatile in nature, it may even be desirable to conduct the entire reaction in a closed vessel, whereby the slightly elevated pressures present are more than sufficient to keep the aforesaid reagent completely in solution. As regards the base to be used as a hydrogen halide acceptor for the reaction, organic tertiary amines are preferred and this category would, of course, normally include such substances as triethylamine, pyridine and the like. Upon completion of the reaction, the desired amide is subsequently isolated from the reaction mixture by first evaporating same to dryness, followed by trituration of the resulting residue with a suitable solvent such as methanol and thereafter subjecting the alcohol solvent filtrate to thick layer chromatography in accordance with the standard techniques of modern analytical chemistry.

The organic halide ($R_2Z$) starting materials used to react with the previously discussed unsubstituted N-(2-thiazolyl)amides in the foregoing alternate route leading to the majority of the compounds of the invention (i.e., those of formula II where $R_2$ is other than hydrogen or cyclooctyl) are, for the most part, known compounds which are either commercially available like benzyl bromide, or else they can easily be synthesized by those skilled in the art starting from readily available materials in accordance with the standard techniques and/or conventional procedures of organic chemistry. For instance, the lower alkyl halides are among the most commonly employed alkylating agents of choice in the laboratory in view of their relative abundance and low cost primarily due to two factors, viz., (1) the ease of HCl addition to olefins and (2) the dehydrochlorination of polychlorinated paraffins, etc. In like manner, the other organic halides, such as the alkenyl halides and aralkyl halides, are also equally readily available.

Inasmuch as many of the N-(2-thiazolyl)amide compounds of this invention possess one asymmetric carbon atom in the acylamino side chain, they may exist in separated d- and l-optically active forms, as well as in racemic dl-mixtures necessarily produced by the various synthetic methods just previously described. The invention, of course, includes the d, l- and racemic forms as all being well within its scope. For instance, an optically active isomer may be obtained by simply resolving the racemic mixture using standard techniques well-known to those skilled in the art, e.g., by fractionally crystallizing an acid addition salt derived from an optically active acid. Alternatively, the optically active isomers may be prepared by using the appropriate enantiomers as starting materials in the foregoing series of reactions.

The pharmaceutically acceptable acid addition salts of the N-(2-thiazolyl)amide base compounds of this invention are prepared by simply treating the aforementioned organic bases with various mineral and organic acids which form non-toxic acid addition salts having pharmacologically acceptable anions, such as the hydrochloride, hydrobromide, hydroiodide, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts. For instance, the salt-formation step may be carried out by using a substantially equimolar amount of the appropriate acid in an aqueous solvent medium or in a suitable organic solvent such as methanol or ethanol. Upon careful evaporation of the solvent, the solid salt product is readily obtained.

As previously indicated, the N-(2-thiazolyl)amide compounds of the present invention are all readily adapted to therapeutic use as anti-inflammatory agents and as immunoregulators, particularly in view of their ability to reduce the swelling and relieve the pain caused by arthritic and other inflammatory disorders that are normally associated with such basic ailments as rheumatoid arthritis and the like. For instance, N-(2-thiazolyl)-α-benzylaminoacetamide, a typical and preferred agent of the present invention, exhibits remarkable activity in the standard carrageenin-induced rat food edema test [described by C. A. Winter et al., *Proc. Soc. Exp. Biol. Med.*, Vol. 111, p. 544 (1962], where it was found to cause a significant (say, for example, 35%) inhibition in swelling at the 1.0 mg./kg. dose level when given by the oral route of administration. More specifically, N-(2-thiazolyl)-α-benzylaminoacetamide has been found to exhibit its aforesaid non-steroidal therapeutic effect in rats when tested orally at levels ranging from 0.33–33 mg./kg., with said compound even retaining its extremely potent anti-inflammatory activity in adrenalectomized animals to a significantly high degree. Additionally, none of these compounds cause substantial side effects to occur in the subject to whom they are so administered, i.e., no problems of toxicity or of a harmful pharmacological nature, either gross or microscopic, are encountered when said compounds are administered for the aforestated purposes in the manner described as indicated above.

In accordance with a method of treatment of the present invention, the herein described N-(2-thiazolyl)amide therapeutic agents can be administered to a host subject via either the oral, parenteral or topical routes of administration. In general, these compounds are most desirably administered in doses ranging from about 10 mg. up to about 1000 mg. per day, although variations will still necessarily occur depending upon the weight of the subject being treated. However, a dosage level that is in the range of from about 0.16 mg. to about 16 mg. per kg. of body weight per day is most desirably employed in order to achieve effective results. Nevertheless, it is still to be appreciated that other variations may also occur in this respect, depending upon the species of animal being treated and its individual response to said medicament, as well as on the particular type of pharmaceutical formulation chosen and the time period and interval at which such administration is carried out. In some instances, dosage levels below the lower limit of the aforesaid range may be more than adequate, while in the other cases still larger doses may be employed without causing any harmful or deleterious side effects to occur provided that such higher dose levels are first divided into several smaller doses that are to be administered throughout the day.

In connection with the use of the N-(2-thiazolyl)amide compounds of this invention for the treatment of a host subject, it is to be noted that they may be administered either alone or in combination with pharmaceutically acceptable carriers by either of the routes previously indicated, and that such administration can be carried out in both single and multiple dosages. More particularly, the novel therapeutic agents of the invention can be administered in a wide variety of different dosage forms, i.e., they may be combined with various pharmaceutically-acceptable inert carriers in the form of tablets, capsules, lozenges, troches, hard candies, powders, sprays, creams, salves, suppositories, jellies, pastes, lotions, ointments, aqueous suspensions, injectable solutions, elixirs, syrups, and the like. Such carriers include solid diluents or fillers, sterile aqueous media and various non-toxic organic solvents, etc. Moreover, such oral pharmaceutical compositiions can be suitably sweetened and/or flavored by means of various agents of the type commonly employed for just such a purpose. In general, the therapeutically-effective compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium sterarate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes, and, if so desired, emulsifying and/or suspending agents as well, together with such diluents as water, ethanol, propylene glycol, glycerin and various like combinations thereof.

For purposes of parenteral administration, solutions of these particular N-(2-thiazolyl)amides in either sesame or peanut oil or in aqueous propylene glycol may be employed, as well as sterile aqueous solutions of the corresponding water-soluble pharmaceutically acceptable acid addition salts previously enumerated. Such aqueous solutions should be suitably buffered if necessary and the liquid diluent first rendered isotonic with sufficient saline or glucose. These particular solutions are especially suitable for intravenous, intramuscular and subcutaneous injection purposes. Additionally, it is also possible to administer the aforesaid N-(2-thiazolyl)amide compounds topically when treating inflammatory conditions of the skin and this may be preferably done by way of creams, jellies, pastes, ointments and the like, in accordance with standard pharmaceutical practice.

The activity of the compounds of the present invention, as anti-inflammatory agents, is best determined by employing the previously mentioned standard carrageenin-induced rat food edema test according to the general procedure described by C. A. Winter et al., as earlier reported in the *Proceedings of the Society of Experimental Biology and Medicine*, Vol. 111, p. 544 (1962). In this test, anti-inflammatory activity is determined as the percent inhibition of edema formation in the hind paw of male albino rats (weighing 150–190 g.) in response to a sub-plantar injection of carrageenin. The carrageenin is injected as a 1% aqueous suspension (0.05 ml.) one hour after oral administration of the drug, which is normally given in the form of an aqueous solution. Edema formation is then assessed three hours after the carrageenin injection by measuring the volume of the injected paw initially as well as at the three-hour mark. The increase in volume three hours after carrageenin injection constitutes the individual response. Compounds are considered active if the response between the drug-treated animals (six rats/group) and the control group (i.e., animals receiving the vehicle alone) is deemed to be significant on comparison with the results afforded by standard compounds like acetylsalicyclic acid at 100 mg./kg. or phenylbutazone at 33 mg./kg., both by the oral route of administration.

On the other hand, the activity of the compounds of the present invention, as immunoregulator agents, is based on a study of their ability to stimulate, in vitro, the lymphocyte proliferation of murine thymus cells cultured in the presence of Concanavalin A (Con A) by employing the general evaluation procedure of V. J. Merluzzi et al., as described in the *Journal of Clinical* and *Experimental Immunology*, Vol. 22, p. 486 (1975). In this study, four different levels of lymphocyte stimulation assay (LSA) activity were established for the compounds undergoing evaluation, viz., those equal to Con A alone; those superior to Con A activity but less than levamisole (taken as the standard compound of choice in this area); those having an activity equal to levamisole; and those having an activity greater than levamisole. Compounds are considered to be active for the present purposes at hand if they are superior to Concanavalin A.

Preparation A

In a 250 ml. three-necked round-bottomed flask equipped with separate dropping funnels, a magnetic stirring apparatus and a thermometer, there were placed 18.7 g. (0.093 mole) of N-benzylglycine hydrochloride in 37.21 ml. of 5 N aqueous sodium hydroxide (0.186 mole or 2 equivalents) with 20 ml. of water later being added, with stirring, to aid in the dissolution. The resulting yellow solution was then cooled to 0° C. with the aid of an ice-water bath. At this point, there were then added simultaneously from two separate dropping funnels 16.3 g. (0.093 mole) of 95% benzyl chloroformate (available from the Aldrich Chemical Company, Inc., Milwaukee, Wisconsin) and 19.5 ml. of 5 N aqueous sodium hydroxide. The addition step was carried out in a dropwise manner (with stirring) and required a time period of 25 minutes. The resulting reaction mixture was stirred at 0° C. for 30 minutes and then at room temperature (~25° C.) for 2.5 hours. Upon completion of this step, a white precipitate formed and the spent mixture, now strongly basic (pH 14), was next extracted with diethyl ether, followed by acidification of the aqueous layer with 12 N hydrochloric acid. The resultant aqueous solution (the solids had all dissolved on acidification) was then extracted with three separate portions of diethyl ether, and the ethereal extracts were subsequently combined, dried over anhydrous sodium sulfate and filtered. The resulting clear filtrate was then concentrated in vacuo to afford a viscous oil, which was subsequently placed under a high vacuum for a period of one hour to yield the desired product in the form of a highly viscous residual oil. In this manner, there were ultimately obtained 21.9 g. (79%) of pure N-benzyloxycarbonyl-N-benzylglycine, which was characterized as such by thin layer chromatography (TLC) as well as by infrared absorption spectroscopy and mass spectroscopy.

Preparation B

The procedure described in Preparation A was used to prepare the following N-benzyloxycarbonylamino acids, starting from the corresponding unprotected amino acid in each instance:
N-benzyloxycarbonylglycine
N-benzyloxycarbonyl-N-methylglycine
N-benzyloxycarbonylalanine
N-benzyloxycarbonyl-N-methylalanine
N-benzyloxycarbonyl-β-phenylalanine
N-benzyloxycarbonyl-α-aminoisovaleric acid
N-benzyloxycarbonylpyrrolidine-2-carboxylic acid
N-benzyloxycarbonylpiperidine-2-carboxylic acid Preparation C The procedure described in Preparation A is repeated here to prepare the following N-benzyloxycarbonylamino acids, starting from the corresponding unprotected amino acids in each case:

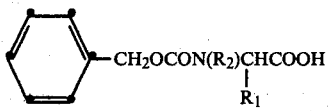

| $R_1$ | $R_2$ |
|---|---|
| n-butyl | hydrogen |
| hydrogen | n-hexyl |
| methyl | isopropyl |
| n-butyl | methyl |
| β-phenylethyl | methyl |
| benzyl | n-butyl |
| hydrogen | allyl |
| hydrogen | methallyl |
| n-butyl | allyl |
| β-phenylethyl | methallyl |
| hydrogen | cyclooctyl |
| methyl | cyclooctyl |
| benzyl | cyclooctyl |
| hydrogen | cyclopentylmethyl |
| n-butyl | cyclohexylmethyl |
| benzyl | cyclohexylmethyl |
| hydrogen | α-naphthylmethyl |
| hydrogen | β-naphthylmethyl |
| hydrogen | 2-picolinyl |
| hydrogen | 3-picolinyl |
| methyl | 4-picolinyl |
| hydrogen | 2-furfuryl |
| hydrogen | 3-furfuryl |
| benzyl | 2-tetrahydrofurfuryl |
| hydrogen | 3-tetrahydrofurfuryl |
| hydrogen | 2-thenyl |
| hydrogen | 3-thenyl |
| methyl | benzyl |
| hydrogen | β-phenylethyl |
| ethyl | γ-phenylpropyl |
| hydrogen | o-fluorobenzyl |
| hydrogen | m-chlorobenzyl |
| isopropyl | p-bromobenzyl |
| hydrogen | m-trifluoromethylbenzyl |
| hydrogen | m-isopropylbenzyl |
| hydrogen | p-ethoxybenzyl |

Preparation D

The procedure described in Preparation A is repeated here to prepare the following N-benzyloxycarbonylamino acids, starting from the corresponding unprotected amino acids in each case:
N-benzyloxycarbonylhomopiperidine-2-carboxylic acid
N-benzyloxycarbonylmorpholine-3-carboxylic acid
N-benzyloxycarbonylthiomorpholine-3-carboxylic acid Preparation E N-(2-Thiazolyl)-α-aminoacetamide was prepared according to the procedure described by J. G. Lombardino in U.S. Pat. No. 3,853,862, starting from 2-aminothiazole and commercially available N-benzyloxycarbonyl-N-methylglycine. It was isolated as the dihydrobromide salt (m.p. 242°–244° C.). The product obtained was identical in every respect with the prior art compound.

EXAMPLE I

In a 50 ml. single-necked round-bottomed flask equipped with a reflux condenser, there were placed 0.5 g. (0.0017 mole) of N-benzyloxycarbonyl-N-benzylglycine (prepared as described in Preparation A) in 10 ml.

of dry tetrahydrofuran and 0.189 g (0.00189 mole) of 2-aminothiazole (available from the Aldrich Chemical Company, Inc., Milwaukee, Wisconsin) in 5 ml. of dry tetrahydrofuran. To this mixture, there was then added 0.52 g. (0.00213 mole) of N-ethoxycarbonyl-2-ethoxy-1,2-dihydroquinoline (also available from Aldrich) dissolved in 10 ml. of dry tetrahydrofuran. The resulting clear yellow solution was then heated to the reflux point for a period of 18 hours. At the end of this time, the reaction mixture was cooled to room temperature (~25° C.) and subsequently concentrated in vacuo to remove the solvent therefrom, followed by the addition of n-hexane to the residue with concomitant stirring at room temperature. After two hours, a solid product formed and the latter material was subsequently recovered by means of suction filtration and washed with a fresh portion of n-hexane to afford pure N'-benzyl-N'-benzyloxycarbonyl-N-(2-thiazolyl)glycineamide.

The above intermediate product was then added to 20 ml. of a 30% solution of hydrogen bromide in glacial acetic acid and the resulting mixture stirred at room temperature for a period of two hours. At this point, the cooled reaction mixture was poured into 100 ml. of diethyl ether and the solid precipitate which formed was thereafter collected by means of suction filtration and dried over phosphorus pentoxide to afford 0.26 g. (46%) of N-(2-thiazolyl)-α-benzylaminoacetamide as the hydrobromide salt, m.p. 220° C. (decomp.). The analytical sample melted at 218° C. (decomp.) after recrystallization from isopropyl alcohol.

Anal. Calcd. for $C_{12}H_{13}N_3OS.1.5HBr$: C, 39.08; H, 4.10; N, 11.39. Found: C, 39.38; H, 4.04; N, 11.19.

EXAMPLE II

The procedure of Example I was employed to prepare the following N-(2-thiazolyl)amides, starting from either 2-aminothiazole or 4-methyl-2-aminothiazole and the appropriate N-benzyloxycarbonylamino acid and proceeding through the corresponding N-benzyloxycarbonylamide intermediate (with subsequent removal of the protecting group) in each instance:

N-(2-thiazolyl)-α-aminoacetamide dihydrobromide, m.p. 265° C. (decomp.)

N-(4-methyl-2-thiazolyl)-α-methylaminoacetamide dihydrobromide monohydrate, m.p. 248° C. (decomp.)

N-(2-thiazolyl)-α-methylaminopropionamide dihydrobromide, m.p. 235° C. (decomp.).

N-(2-thiazolyl)-α-aminoisovaleramide dihydrobromide monohydrate, m.p. 242° C. (decomp.)

N-(4-methyl-2-thiazolyl)-α-aminoisovaleramide dihydrobromide, m.p. 240° C. (decomp.)

N-(4-methyl-2-thiazolyl)-α-amino-β-phenylpropionamide dihydrobromide, m.p. 248° C. (decomp.)

N-(2-thiazolyl)-α-aminopropionamide hydrobromide 0.125 hydrate, m.p. 242° C. (decomp.)

N-(4-methyl-2-thiazolyl)-α-aminopropionamide dihydrobromide, m.p. 256° C. (decomp.)

N-(2-thiazolyl)pyrrolidine-2-carboxamide dihydrobromide, m.p. 207° C. (decomp.)

N-(2-thiazolyl)piperidine-2-carboxamide hydrobromide, m.p. 246° C. (decomp.)

N-(4-methyl-2-thiazolyl)piperidine-2-carboxamide dihydrobromide, m.p. 228° C. (decomp.).

EXAMPLE III

In a 100 ml. single-necked round-bottomed flask, there was placed 0.50 g. (0.00157 mole) of N-(2-thiazolyl)-α-aminoacetamide dihydrobromide (the first compound reported in Example II) and after the system had been cooled in an ice-water bath, 31.4 ml. of 0.1 N aqueous sodium hydroxide (0.00314 mole) was slowly added thereto with constant agitation being maintained throughout the addition step. Upon completion of the alkaline addition, the pH of the resulting mixture was pH 9.5 and the clear solution obtained was then filtered and evaporated to dryness in a rotary, using only a slight amount of heat from the water bath, to give a white solid material as residue. This particular material was then triturated four times with fresh portions (15 ml. each) of refluxing diethyl ether, and the latter extracts were subsequently combined and evaporated to dryness in the usual manner to afford 30 mg. of a white solid, which proved to be pure N-(2-thiazolyl)-α-aminoacetamide (as the free base) as determined by thin-layer chromatography (TLC). An additional 22 mg. of this same material was later obtained by triturating the ether-insoluble off-white solid with three-20 ml. portions of refluxing acetone, followed by rotary evaporation of the solvent in the same manner as before. The total yield of pure N-(2-thiazolyl)-α-aminoacetamide was therefore 52 mg. (22%).

EXAMPLE IV

The procedure described in Example III is repeated to prepare the other free base compounds of this invention reported as the hydrobromide salts in Examples I-II by merely employing the appropriate N-(2-thiazolyl)amide salt as the starting material of choice in place of N-(2-thiazolyl)-α-aminoacetamide dihydrobromide, using the same molar proportions as before. In this way, N-(2-thiazolyl)-α-benzylaminoacetamide 1.5 hydrobromide (the product of Example I) is converted to the corresponding free organic base compound, as are all the other N-(2-thiazolyl)amide salts of Example II.

EXAMPLE V

The following N-(2-thiazolyl)amides are prepared by employing the procedures of Examples I and III, starting from the corresponding 2-aminothiazole compound and the appropriate N-benzyloxycarbonylamino acid in each instance:

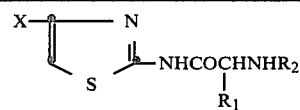

| X | $R_1$ | $R_2$ |
|---|---|---|
| $C_2H_5$ | H | hydrogen |
| H | $n\text{-}C_4H_9$ | hydrogen |
| H | $C_6H_5CH_2$ | hydrogen |
| $CH_3$ | $n\text{-}C_4H_9$ | hydrogen |
| H | H | n-hexyl |
| $n\text{-}C_6H_{13}$ | H | methyl |
| H | $CH_3$ | isopropyl |
| H | $n\text{-}C_4H_9$ | methyl |
| H | $C_6H_5CH_2CH_2$ | methyl |
| $CH_3$ | $C_6H_5CH_2$ | n-butyl |
| $CH_3$ | H | allyl |
| H | H | methallyl |
| H | $n\text{-}C_4H_9$ | allyl |
| H | $C_6H_5CH_2CH_2$ | methallyl |
| $CH_3$ | H | cyclooctyl |
| H | $CH_3$ | cyclooctyl |
| H | $C_6H_5CH_2$ | cyclooctyl |
| $C_2H_5$ | H | cyclopentylmethyl |
| H | $n\text{-}C_4H_9$ | cyclohexylmethyl |
| H | $C_6H_5CH_2$ | cycloheptylmethyl |

-continued

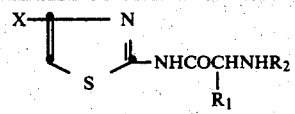

| X | R₁ | R₂ |
|---|---|---|
| H | H | α-naphthylmethyl |
| CH₃ | H | β-naphthylmethyl |
| H | H | 2-picolinyl |
| n-C₃H₇ | H | 3-picolinyl |
| H | CH₃ | 4-picolinyl |
| CH₃ | H | 2-furfuryl |
| H | H | 3-furfuryl |
| H | C₆H₅CH₂ | 2-tetrahydrofurfuryl |
| CH₃ | H | 3-tetrahydrofurfuryl |
| C₂H₅ | H | 2-thenyl |
| H | H | 3-thenyl |
| H | CH₃ | benzyl |
| iso-C₃H₇ | H | benzyl |
| H | H | β-phenylethyl |
| H | C₂H₅ | γ-phenylpropyl |
| CH₃ | H | o-fluorobenzyl |
| H | H | m-chlorobenzyl |
| H | iso-C₃H₇ | p-bromobenzyl |
| C₂H₅ | H | m-trifluoromethylbenzyl |
| H | H | m-isopropylbenzyl |
| CH₃ | H | p-ethoxybenzyl |
| H | CH₃ | p-(n-propoxy)benzyl |
| H | H | 3,4-ethylenedioxybenzyl |

EXAMPLE VI

The following N-(2-thiazolyl)amides are prepared by employing the procedures of Examples I and III, starting from the corresponding 2-aminothiazole compound and the appropriate N-benzyloxycarbonylamino acid in each instance:

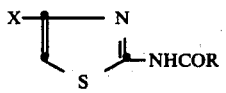

| X | R |
|---|---|
| CH₃ | 2-pyrrolidinyl |
| iso-C₃H₇ | 2-pyrrolidinyl |
| n-C₅H₁₁ | 2-pyrrolidinyl |
| n-C₆H₁₃ | 2-pyrrolidinyl |
| C₂H₅ | 2-piperidyl |
| n-C₄H₉ | 2-piperidyl |
| n-C₆H₁₃ | 2-piperidyl |
| H | 2-homopiperidyl |
| CH₃ | 2-homopiperidyl |
| n-C₃H₇ | 2-homopiperidyl |
| n-C₆H₁₃ | 2-homopiperidyl |
| H | 3-morpholinyl |
| CH₃ | 3-morpholinyl |
| C₂H₅ | 3-morpholinyl |
| iso-C₄H₉ | 3-morpholinyl |
| n-C₆H₁₃ | 3-morpholinyl |
| H | 3-thiomorpholinyl |
| CH₃ | 3-thiomorpholinyl |
| iso-C₃H₇ | 3-thiomorpholinyl |
| n-C₅H₁₁ | 3-thiomorpholinyl |
| n-C₆H₁₃ | 3-thiomorpholinyl |

EXAMPLE VII

In a 50 ml. round-bottomed flask equipped with reflux condenser, there were placed 1.0 g. (0.0045 mole) of 2-(bromoacetylamino)thiazole [*Chemical Abstracts,* Vol. 51, p. 164356 (1957)] in 20 ml. of acetone together with 1.13 g. (0.0106 mole) of benzylamine (available from Eastman Kodak Company of Rochester, N.Y.). The resulting clear solution was then heated to the reflux point for a period of two hours. At the end of this time, the reaction mixture was cooled to ambient temperatures in an ice water bath and the acetone solvent was subsequently removed therefrom by means of evaporation under reduced pressure. The residue so obtained was then extracted with three-50 ml. portions of hot diethyl ether and the latter extracts were subsequently combined, cooled and thereafter acidified with anhydrous hydrochloric acid (using dry hydrogen chloride gas). The oily residue which formed at this point was then triturated with a minimum amount of absolute ethanol, transforming the oil to a solid which was subsequently cooled and filtered. After drying the latter material to constant weight over phosphorus pentoxide, there was ultimately obtained 1.0 g (67%) of pure N-(2-thiazolyl)-α-benzylaminoacetamide hydrochloride, m.p. 234°–235° C. (decomp.). The melting point of the analytical sample was raised to 238° C. (decomp.) after two recrystallizations from pure methanol.

Anal. Calcd. for $C_{12}H_{13}N_3OS \cdot HCl$: C, 50.79; H, 4.97; N, 14.81. Found: C, 50.40; H, 4.94; N, 14.74.

EXAMPLE VIII

The procedure described in Example VII was essentially followed except that 2.0 g. (0.009 mole) of 2-(bromoacetylamino)thiazole [*Chemical Abstracts,* Vol. 51, p. 164356 (1957)] and 2.04 g. (0.018 mole) of freshly-distilled 2-thenylamine (available from Fairfield Chemical of Baltimore, Md.) were the starting materials employed. The reaction mixture was refluxed for a period of three hours and the desired product was isolated as the hydrobromide salt by using dry gaseous hydrogen bromide as the acidifying agent. In this manner, there were ultimately obtained 27.0 g. (23%) of N-(2-thiazolyl)-α-(2-thenylamino)acetamide 1.5 hydrobromide, m.p. 222° C. (decomp.). The melting point of the analytical sample was raised to 226° C. (decomp.) after one recrystallization from ethanol.

Anal. Calcd. for $C_{10}H_{11}N_3OS \cdot 1.5HBr$: C, 32.04; H, 3.36; N, 11.21. Found: C, 32.48; H, 3.44; N, 11.22.

EXAMPLE IX

The procedure of Example VII was employed to prepare the following N-(2-thiazolyl)-α-aminoacetamides, starting from the corresponding 2-(bromoacetylamino)thiazole and using the appropriate organic amine reagent in each instance:

N-(2-thiazolyl)-α-ethylaminoacetamide 1.75 hydrobromide, m.p. 211° C. (decomp.)

N-(2-thiazolyl)-α-(n-propylamino)acetamide 1.75 hydrobromide, m.p. 224° C. (decomp.)

N-(2-thiazolyl)-α-(n-butylamino)acetamide 1.88 hydrobromide, m.p. 200° C. (decomp.)

N-(2-thiazolyl)-α-allylaminoacetamide hydrobromide, m.p. 196° C. (decomp.)

N-(2-thiazolyl)-α-cyclooctylaminoacetamide hydrobromide, m.p. 238° C. (decomp.)

N-(2-thiazolyl)-α-cyclohexylmethylaminoacetamide hydrochloride, m.p. 235°–236° C. (decomp.)

N-(2-thiazolyl)-α-(2-furfurylamino)acetamide hydrobromide, m.p. 200° C. (decomp.)

N-(2-thiazolyl)-α-(2-tetrahydrofurfurylamino)acetamide 1.67 hydrochloride, m.p. 188°–192° C. (decomp.)

N-(4-methyl-2-thiazolyl)-α-benzylaminoacetamide dihydrochloride, m.p. 229° C. (decomp.)

N-(2-thiazolyl)-α-(p-fluorobenzylamino)acetamide hydrochloride, m.p. 229° C. (decomp.)

N-(2-thiazolyl)-α-(p-chlorobenzylamino)acetamide hydrochloride, m.p. 227° C. (decomp.)

N-(2-thiazolyl)-α-(p-methylbenzylamino)acetamide hydrochloride, m.p. 225° C. (decomp.)

N-(2-thiazolyl-α-(p-trifluoromethylbenzylamino)acetamide 1.8 hydrochloride, m.p. 228°–229° C. (decomp.)

N-(2-thiazolyl)-α-(p-methoxybenzylamino)acetamide hydrochloride, m.p. 216° C. (decomp.)

N-(2-thiazolyl)-α-(3,4-methylenedioxybenzylamino)acetamide hydrochloride, m.p. 231°–233° C. (decomp.)

N-(2-thiazolyl)-α-(β-phenylethylamino)acetamide hydrochloride hydrate, m.p. 223° C. (decomp.)

N-(4-methyl-2-thiazolyl)-α-(β-phenylethylamino)acetamide hydrochloride 0.25 hydrate, m.p. 214° C. (decomp.).

EXAMPLE X

The free base compounds corresponding to the hydrochloride and hydrobromide salts reported in Examples VII–IX are prepared by treating an aqueous solution of the appropriate N-(2-thiazolyl)amide salt with an equivalent amount in moles of sodium hydroxide in accordance with the procedure of Example III. In this way, N-(2-thiazolyl)-α-(2-thenylamino)acetamide 1.5 hydrobromide (the product of Example VIII) is converted to the corresponding free organic base compound, as are all the other N-(2-thiazolyl)amide salts reported in Examples VII and IX, respectively.

EXAMPLE XI

The compounds reported as bases in Example V, except for those where $R_1$ in the structural formula is other than hydrogen, are also prepared by using the procedure of Example VII (instead of Example I), starting from the corresponding 2-(bromoacetylamino)-thiazole and the appropriate organic amine ($R_2NH_2$) reagent in each instance.

EXAMPLE XII

To a well-stirred solution at room temperature (~25° C.) consisting of 250 mg. (0.0159 mole) of N-(2-thiazolyl)-α-aminoacetamide dissolved in 25 ml. of ethanol containing 70 mg. (0.00069 mole) of triethylamine, there was added in a dropwise manner over a period of 45 minutes 0.064 ml. (0.089 g., 0.00052 mole) of benzyl bromide dissolved in 5.0 ml. of diethyl ether. The reaction mixture was then stirred at ambient temperatures for a period of 15 minutes, followed by refluxing overnight for a period of approximately 16 hours. At this point, the resulting mixture was treated with an additional 0.064 ml. (0.089 g., 0.00052 mole) of benzyl bromide in the same manner as before, followed by a 5.5 hour reflux of the final mixture so obtained. Upon completion of this step, the spent reaction mixture was cooled to room temperature and rotary evaporated to dryness while under reduced pressure to give a damp yellow solid as residue. This latter material was then triturated with approximately 10 ml. of methanol and the insoluble white solid so obtained was subsequently removed from the mixture by means of filtration.

The resulting clear methanol filtrate containing the desired product was then subjected to thick layer chromatography by streaking same on four 20×20 cm. silica gel plates (with a layer thickness of 2 mm.) using a chloroform-methanol (4:1 by volume) solvent system. An authentic sample of the desired product was also streaked in the same manner as indicated above for comparison purposes. The four bands so obtained were then carefully removed by scraping and thereafter triturated with three separate portions of fresh boiling methanol. After filtering the latter methanol filtrate by passing same through kieselguhr to remove any dissolved silica gel, the clear filtrate was subsequently evaporated to dryness in a rotary evaporator using a pre-weighed flask for the present purposes at hand. In this manner, there was ultimately obtained ~60 mg. of crude N-(2-thiazolyl)-α-benzylaminoacetamide as the free base compound.

A solution of the free organic base in diethyl ether was next prepared by dissolving same in ~50 ml. of the latter solvent while at the reflux point. This was accomplished by first allowing the ethereal mixture to stir at room temperature for a period of approximately 16 hours (overnight), followed by a brief heating to reflux and then filtration. After rinsing the filter cake with hot diethyl ether, the filtrate and washings were combined and thereafter cooled to room temperature. The resulting ethereal solution was then acidified with anhydrous hydrochloric acid by bubbling dry hydrogen chloride gas into the mixture, with stirring, until saturation of same with respect to said gas (and concomitant precipitation) was substantially complete. The ether solvent was then removed by means of a stream of nitrogen and the residual semi-solid mass was taken up in 2 ml. of methanol and 3 ml. of ethanol with the aid of gentle heating. Upon filtration of the latter solution, followed by concentration of the resulting filtrate to a volume of ~2 ml., there was obtained a lower alkanolic concentrate of the desired product. This concentrate was then gradually heated with small portions of ethanol while being constantly refluxed so as to increase the concentration of the latter solvent over that of the methanol. When the final volume reached ~1 ml., the mixture was slowly cooled to room temperature, followed by further cooling in an ice bath. The crystals so obtained were thereafter recovered by means of suction filtration, washed successively with fresh portions of ethanol and methanol and dried in vacuo to constant weight over phosphorus pentoxide to afford 20 mg. (6.8%) of pure N-(2-thiazolyl)-α-benzylaminoacetamide hydrochloride, m.p. 218°–220° C. (decomp.). On admixture with an authentic sample (viz., the product of Example VI), no depression in melting point could be observed (mixed m.p. 224°–226° C.).

EXAMPLE XIII

The N-(2-thiazolyl)amides reported in Examples II, V and VIII–IX, other than those where $R_2$ in the structural formula is hydrogen or cyclooctyl, are also prepared by the procedure of Example XII (instead of using Example I), starting from the corresponding unsubstituted N-(2-thiazolyl)-amide (where $R_2$ in the structural formula is hydrogen) and the appropriate organic chloride, bromide or iodide ($R_2Cl$, $R_2Br$ or $R_2I$) as the case may be in each instance.

EXAMPLE XIV

The non-toxic hydrohalide acid addition salts of each of the previously reported N-(2-thiazolyl)amide base compounds of this invention, such as the corresponding novel hydrochloride, hydrobromide and hydriodide salts, are each individually prepared by first dissolving the respective organic base compound in absolute ether followed by the introduction of the appropriate hydrohalide gas into the reaction solution until saturation of same is complete with respect to said gas, whereupon the desired acid addition salt soon precipitates from said solution. In this way, 5.0 g. of N-(2-thiazolyl)-α-(2-thenylamino)acetamide obtained as a free base product in Example X, is converted via dry hydrogen chloride gas to the corresponding hydrochloride acid addition salt in substantially quantitative yield.

EXAMPLE XV

The nitrate, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluene sulfonate salts of each of the aforementioned N-(2-thiazolyl)amide base compounds reported previously are each prepared by dissolving the proper molar amounts of the respective acid and base in separate portions of ethanol and then mixing the two solutions together, followed by the addition of diethyl ether to the resultant mixture in order to effect precipitation of the desired acid addition salt therefrom. In this manner, equimolar amounts of N-(2-thiazolyl)-α-benzylaminoacetamide and concentrated sulfuric acid react to afford the corresponding sulfuric acid addition salt. In like manner, each of the other salts is prepared.

EXAMPLE XVI

A dry solid pharmaceutical composition is prepared by blending the following materials together in the proportions by weight specified below:

| | |
|---|---|
| N-(2-Thiazolyl)-α-benzylaminoacetamide hydrochloride | 50 |
| Sodium citrate | 25 |
| Alginic acid | 10 |
| Polyvinylpyrrolidone | 10 |
| Magnesium stearate | 5 |

After the dried composition is thoroughly blended, tablets are punched from the resulting mixture, each tablet being of such size that it contains 100 mg. of the active ingredient. Other tablets are also prepared in a similar fashion containing 5, 10, 25 and 50 mg. of the active ingredient, respectively, by merely using the appropriate amount of the N-(2-thiazolyl)amide salt in each case.

EXAMPLE XVII

A dry solid pharmaceutical composition is prepared by combining the following materials together in the proportions by weight indicated below:

| | |
|---|---|
| N-(2-Thiazolyl)α(2-thenylamino) acetamide 1.5 hydrobromide | 50 |
| Calcium carbonate | 20 |
| Polyethylene glycol, average molecular weight, 4000 | 30 |

The dried solid mixture so prepared is then thoroughly agitated so as to obtain a powdered product that is completely uniform in every respect. Soft elastic and hard-filled gelatin capsule containing this pharmaceutical composition are then prepared, employing a sufficient quantity of material in each instance so as to provide each capsule with 250 mg. of the active ingredient.

EXAMPLE XVIII

The following N-(2-thiazolyl)amides reported in Examples I–II and VII–IX, as well as in Preparation E, were evaluated for their ability to stimulate, in vitro, the lymphocyte proliferation of murine thymus cells cultured in the presence of Concanavalin A (Con A) by employing the procedure of V. J. Merluzzi et al., as essentially described in the *Journal of Clinical and Experimental Immunology*, Vol. 22, p. 486 (1975). The cells were derived from male C57B1/6 mice of from 6–8 weeks age, purchased from the Jackson Laboratories of Bar Harbor, Maine and the Con A was obtained from Sigma Chemicals of St. Louis, Missouri. Each cell culture (consisting of 0.10 ml. thymus cells stock solution, 0.05 ml. of Con A stock solution and 0.05 ml. of drug solution) was performed in quadruplicate and cellular proliferation was measured, after 48 hours of incubation at 37° C., by pulsing each culture with $^3$H-thymidine (0.01 ml. of specific activity 1.9 C/mM, obtained from Schwarz-Mann, Inc. of Orangeburg, N.Y.) and then determining the incorporation of $^3$H-thymidine into cellular desoxyribonucleic acid (DNA) by an assessment of radioactivity using a liquid scintillation counter. The results obtained in this manner are expressed quantitatively in terms of the average counts per minute (cpm) of $^3$H-thymidine incorporated at the drug level with maximum activity by the quadruplicate cell cultures. On this basis, four different levels of activity were established in the present lymphocyte stimulation assay (LSA) and these are defined in the manner hereinafter indicated, viz., those levels equal to Con A alone (6,000±300 cpm) were assigned a negative value or score of zero; those superior to Con A activity but less than levamisole (10,000±700 cpm) were scored as +; while those equal to levamisole (22,000±900 cpm) were scored as + + and those having an activity greater than levamisole (27,000±1,000 cpm) were scored as + + + for the present purposes at hand. In this way, the table below illustrates the results obtained with each compound:

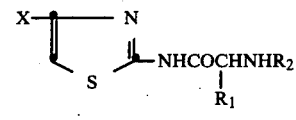

| X | $R_1$ | $R_2$ | LSA Activity |
|---|---|---|---|
| H | H | hydrogen | + + |
| H | $CH_3$ | hydrogen | + + + |
| $CH_3$ | $CH_3$ | hydrogen | + + + |
| H | iso-$C_3H_7$ | hydrogen | + + |
| $CH_3$ | iso-$C_3H_7$ | hydrogen | + + + |
| $CH_3$ | $C_6H_5CH_2$ | hydrogen | + + + |
| H | H | methyl | + + + |
| $CH_3$ | H | methyl | + + + |
| H | $CH_3$ | methyl | + + + |
| H | H | ethyl | + + + |
| H | H | n-propyl | + + |
| H | H | n-butyl | + + |
| H | H | allyl | + + |
| H | H | cyclooctyl | + + |
| H | H | cyclohexylmethyl | + + |
| H | H | 2-furfuryl | + + |
| H | H | 2-tetrahydrofurfuryl | + + |
| H | H | 2-thenyl | + + + |
| H | H | benzyl | + + + |
| $CH_3$ | H | benzyl | + + + |

-continued

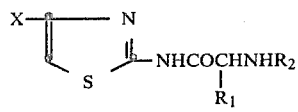

| X | R₁ | R₂ | LSA Activity |
|---|----|----|--------------|
| H | H | p-fluorobenzyl | +++ |
| H | H | p-chlorobenzyl | ++ |
| H | H | p-trifluoromethylbenzyl | ++ |
| H | H | p-methylbenzyl | + |
| H | H | p-methoxybenzyl | +++ |
| H | H | 3,4-methylenedioxybenzyl | ++ |
| H | H | β-phenylethyl | ++ |
| CH₃ | H | β-phenylethyl | +++ |

EXAMPLE XIX

The lymphocyte stimulation assay (LSA) procedure described in Example XVIII was employed again to evaluate the immune response activity (in vitro) of the following N-(2-thiazolyl)amides (in the form of their hydrobromide salts), and the results obtained in this manner are reported below in the table as shown:

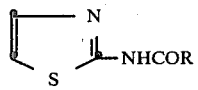

| X | R | LSA Activity |
|---|---|--------------|
| H | 2-pyrrolidinyl | +++ |
| H | 2-piperidyl | +++ |
| CH₃ | 2-piperidyl | +++ |

EXAMPLE XX

The following N-(2-thiazolyl)amides were tested for anti-inflammatory activity in rats, using the standard carrageen-ininduced rat food edema test, according to the procedure essentially described by C. A. Winter et al., as first reported in the *Proceedings of the Society for Experimental Biology and Medicine*, Vol. 111, p. 544 (1962). The compounds were administered orally in the form of their previously reported hydrohalide salts at a dose level of 33 mg./kg. The results obtained in this manner are presented in the table below in terms of the percent inhibition of edema formation afforded by each test compound as compared to the control (i.e., aqueous solution with no compound):

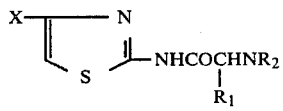

| X | R₂ | % Inhibition |
|---|----|--------------|
| H | methyl | 54 |
| CH₃ | methyl | 53 |
| H | benzyl | 52 |
| H | p-fluorobenzyl | 48 |
| H | β-phenylethyl | 53 |

EXAMPLE XXI

The test procedure employed in the previous example was used again to determine the anti-inflammatory activity of the following N-(2-thiazolyl)amides (in the form of their hydrobromide salts), and the results obtained in this manner are reported below in the usual tabular form:

| R | % Inhibition |
|---|--------------|
| 2-pyrrolidinyl | 48 |
| 2-piperidinyl | 55 |

EXAMPLE XXII

The test procedure employed in Example XX was repeated again to determine the anti-inflammatory activity of N-(2-thiazolyl)-α-benzylaminoacetamide hydrochloride (product of Example VII) at dosages below 33 mg./kg., and the results obtained with this compound are reported in the table below at three different concentration levels:

| Dose (mg./kg.) | % Inhibition |
|----------------|--------------|
| 10 | 54 |
| 3.3 | 47 |
| 1.0 | 35 |

What is claimed is:

1. A compound of the formula:

$$\text{X}\underset{S}{\overset{}{\underset{\|}{\bigsqcup}}}\overset{N}{\underset{}{\bigsqcup}}\text{—NHCOCHNR}_2 \quad \text{II}$$
$$\qquad\qquad\qquad\qquad\quad R_1$$

and the pharmaceutically acceptable acid addition salts thereof, wherein
X is a member selected from the group consisting of hydrogen and alkyl having from one to six carbon atoms;
R₁ is a member selected from the group consisting of hydrogen, alkyl having from one to four carbon atoms, benzyl and β-phenylethyl; and
R₂ is a member selected from the group consisting of hydrogen, cyclooctyl, cycloalkylmethyl having from five to seven carbon atoms in the cycloalkyl moiety, naphthylmethyl, picolinyl, furfuryl, tetrahydrofurfuryl, thenyl, phenylalkyl and ring-substituted phenylalkyl each having up to three carbon atoms in the alkyl moiety wherein said ring substituent, when divalent, is lower alkylenedioxy directly attached to adjacent positions of the phenyl ring and when monovalent is a member chosen from the group consisting of fluorine, chlorine, bromine, trifluoromethyl, lower alkyl and lower alkoxy; said R₂ being other than hydrogen when said R₁ is hydrogen or alkyl having from one to four carbon atoms.

2. A compound as claimed in claim 1 of the formula II wherein X is hydrogen, R₁ is hydrogen and R₂ is phenylalkyl having up to three carbon atoms in the alkyl moiety.

3. A compound as claimed in claim 2 wherein R₂ is benzyl.

4. A compound as claimed in claim 1 of the formula II wherein X is hydrogen, $R_1$ is hydrogen and $R_2$ is ring-substituted phenylalkyl having up to three carbon atoms in the alkyl moiety.

5. A compound as claimed in claim 4 wherein $R_2$ is p-fluorobenzyl.

6. A compound as claimed in claim 4 wherein $R_2$ is p-(lower alkoxy)benzyl.

7. A compound as claimed in claim 6 wherein $R_2$ is p-methoxybenzyl.

8. A compound as claimed in claim 1 of the formula II wherein X is alkyl having from one to six carbon atoms, $R_1$ is hydrogen and $R_2$ is phenylalkyl having up to three carbon atoms in the alkyl moiety.

9. A compound as claimed in claim 8 wherein X is methyl and $R_2$ is benzyl.

10. A compound as claimed in claim 8 wherein X is methyl and $R_2$ is $\beta$-phenylethyl.

11. A compound as claimed in claim 1 of the formula II wherein X is hydrogen, $R_1$ is hydrogen and $R_2$ is thenyl.

12. A compound as claimed in claim 1 of the formula II wherein X is hydrogen, $R_1$ is hydrogen and $R_2$ is tetrahydrofurfuryl.

13. A compound as claimed in claim 1 of the formula II wherein X is hydrogen, $R_1$ is benzyl and $R_2$ is hydrogen.

14. A compound as claimed in claim 1 of the formula II wherein X is alkyl having from one to six carbon atoms, $R_1$ is benzyl and $R_2$ is hydrogen.

15. A compound as claimed in claim 14 wherein X is methyl.

16. N-(2-Thiazolyl)-$\alpha$-benzylaminoacetamide.

17. N-(2-Thiazolyl)-$\alpha$-(2-thenylamino)acetamide.

18. N-(4-Methyl-2-thiazolyl)-$\alpha$-amino-$\beta$-phenylpropionamide.

19. A pharmaceutical composition suitable for alleviating inflamatory conditions and regulating body immune responses comprising a pharmaceutically acceptable carrier and a therapeutically-effective amount of a compound of the formula:

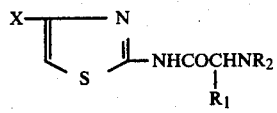

and the pharmaceutically acceptable acid addition salts thereof, wherein

X is a member selected from the group consisting of hydrogen and alkyl having from one to six carbon atoms;

$R_1$ is a member selected from the group consisting of hydrogen, alkyl having from one to four carbon atoms, benzyl and $\beta$-phenylethyl; and $R_2$ is a member selected from the group consisting of hydrogen, alkyl having from one to six carbon atoms, allyl, methallyl, cyclooctyl, cycloalkylmethyl having from five to seven carbon atoms in the cycloalkyl moiety, naphthylmethyl, picolinyl, furfuryl, tetrahydrofurfuryl, thenyl, phenylalkyl and ring-substituted phenylalkyl each having up to three carbon atoms in the alkyl moiety wherein said ring substituent, when divalent, is methylenedioxy or ethylenedioxy directly attached to adjacent positions of the phenyl ring and when monovalent is a member chosen from the group consisting of fluorine, chlorine, bromine, trifluoromethyl, lower alkyl and lower alkoxy.

20. The composition according to claim 19 wherein the compound is N-(2-thiazolyl)-$\alpha$-methylaminoacetamide.

21. The composition according to claim 19 wherein the compound is N-(2-thiazolyl)-$\alpha$-benzylaminoacetamide.

22. The composition according to claim 19 wherein the compound is N-(2-thiazolyl)-$\alpha$-(p-fluorobenzylamino)acetamide.

23. The composition according to claim 19 wherein the compound is N-(2-thiazolyl)-$\alpha$-(2-thenylamino)acetamide.

24. The composition according to claim 19 wherein the compound is N-(4-methyl-2-thiazolyl)-$\alpha$-amino-$\beta$-phenylpropionamide.

* * * * *